United States Patent [19]

Sabol et al.

[11] 4,201,682
[45] May 6, 1980

[54] METHOD OF PREPARING OVERBASED MAGNESIUM SULFONATES

[75] Inventors: Albert R. Sabol, Munster, Ind.; Dennis G. Petrille, Naperville; Edward W. Heffern, Schaumburg, both of Ill.

[73] Assignee: Standard Oil Company (Indiana), Chicago, Ill.

[21] Appl. No.: 625,302

[22] Filed: Oct. 24, 1975

Related U.S. Application Data

[63] Continuation of Ser. No. 316,843, Dec. 20, 1972, abandoned.

[51] Int. Cl.² .............................................. C10M 1/40
[52] U.S. Cl. ...................................... 252/33.4; 252/25
[58] Field of Search .................... 252/18, 25, 33, 33.4; 44/51

[56] References Cited

U.S. PATENT DOCUMENTS

| | | |
|---|---|---|
| 3,629,109 | 12/1971 | Gergel et al. ........................ 252/33 |
| 3,761,411 | 9/1973 | Dickey .............................. 252/25 X |
| 3,853,774 | 12/1974 | Crocker ............................ 252/18 X |
| 3,865,737 | 2/1975 | Kemp ................................ 252/18 X |

*Primary Examiner*—Andrew Metz
*Attorney, Agent, or Firm*—Edwin C. Lehner; Arthur G. Gilkes; William T. McClain

[57] ABSTRACT

Over-based oil-soluble magnesium sulfonate compositions are formed by one-step carbonation of a reactant mixture containing magnesium hydroxide formed in situ.

8 Claims, No Drawings

METHOD OF PREPARING OVERBASED MAGNESIUM SULFONATES

CROSS REFERENCE TO RELATED APPLICATION

This is a continuation of application Ser. No. 316,843, filed Dec. 20, 1972, now abandoned.

BACKGROUND OF THE INVENTION

1. Field of the Invention

This invention relates to the preparation of over-based oil-soluble magnesium sulfonates containing excess magnesium a magnesium carbonate.

2. Prior Art

The over-based oil-soluble magnesium sulfonates prepared in accordance with this invention are products well known in the sulfonate art and are widely used as additives in lubricants and fuels. Preparation of these products by available techniques generally requires at least two treatments with carbon dioxide in order to effectively convert the basic magnesium compound such as magnesium oxide used as the magnesium source to magnesium carbonate which is formed in situ in the mixture undergoing carbonation. A one-step carbonation process is desired for it reduces the processing cost of the products.

SUMMARY OF THE INVENTION

A simplified procedure has been discovered that utilizes magnesium oxide as the source of magnesium in the over-based oil-soluble magnesium sulfonates described herein, and only requires one carbonation step to achieve the formation in situ of the desired amount of magnesium carbonate in the product. In accordance with the invention, the method of preparing over-based oil-soluble magnesium sulfonate compositions comprises the steps of: heating a reactant mixture comprising (a) an amount of an oil-soluble sulfonate anion-affording material sufficient to provide about 10–40 weight oil-soluble magnesium sulfonate in said composition, said material containing molar proportions of about 0.1–1.0 mol oil-soluble ammonium sulfonate, 0 to about 0.9 mol neutral oil-soluble magnesium sulfonate, and 0 to about 0.9 mol oil-soluble sulfonic acid, said reactant (a) further characterized as containing at least 0.1 mol of said ammonium sulfonate per mole of magnesium oxide in said mixture, (b) an amount of magnesium oxide in excess of the stoichiometric amount required for neutral magnesium sulfonate formation, (c) about 0.2 to about 1.0 mol of an alkanol having 1 to 4 carbons atoms per mol of magnesium oxide, (d) about 0.5 to 2.25 mols water per mol of magnesium oxide, and (e) an inert hydrocarbon diluent, at a temperature in the range of about 175° to 200° F. under refluxing conditions at atmospheric pressure for a period of time sufficient to convert said magnesium oxide to magnesium hydroxide in said mixture; and then treating the mixture with carbon dioxide for a period of time sufficient to convert said magnesium hydroxide to magnesium carbonate.

The present invention is based on the discovery that magnesium oxide in a reactant mixture containing a sulfonate anion-affording material, an alkanol having 1 to 4 carbon atoms, water and an inert hydrocarbon diluent can be converted to magnesium hydroxide, for subsequent reaction in one-step with carbon dioxide, in situ when the reactant mixture contains at least 0.1 mol of ammonium sulfonate per mol of magnesium oxide in the mixture.

The sulfonate anion-affording material can be all ammonium sulfonate or a mixture of ammonium sulfonate with either the same or a different sulfonic acid or with a preformed neutral magnesium sulfonate having the same or different sulfonate moiety or with both of said sulfonic acid and magnesium sulfonate. It is to be understood that the ammonium sulfonate becomes all or a portion of the neutral magnesium sulfonate in the over-based product.

The magnesium oxide used in the process of this invention is the highly active material known in the art. It should have an iodine number, indicative of reactivity in the range of 65–140. Time of conversion to the magnesium hydroxide during the heating step of the process of this invention is dependent upon the reactivity of the magnesium oxide. For example, when the iodine number is about 65–70, the heating and refluxing step will be about 60 to 90 minutes, for oxide having 70–100 iodine number it will be about 30 minutes and for the highly reactive oxide in the range of 100–140 it will be about 10 to 15 minutes. Completion of the conversion of the oxide to hydroxide is noted by a visual change in the capacity of the mixture from a milky to about a crystal clear appearance. The mixture is then ready for carbonation.

Carbonation, i.e., treatment with carbon dioxide, of the mixture is at a temperature in the range of about 100° to 160° F., preferably 110° to 130° F., until the reaction with magnesium hydroxide ceases.

Viscosity control of the reactant mixtures is achieved by use of an inert hydrocarbon solvent or diluent. The amount of diluent is only that amount that is necessary to provide a suitable viscosity in the mixture to facilitate the reactions. A suitable diluent is a low viscosity mineral oil containing either benzene, xylene or toluene which can be removed after carbonation so that the product recovered contains the mineral oil as the vehicle. A light petroleum fraction, such as kerosene or light catalytic cycle oil may be used when the over-based product is used as an additive in hydrocarbon fuels such as residual oils, distillate and diesel fuels and gasoline.

The ammonium alkenyl sulfonates described herein are unique oil-soluble materials which are substantially free of hydroxy alkyl sulfonates and are useful as lubricant and fuel additives. It has been found that they can be used as the source of the magnesium sulfonate in the over-based products of this invention. The oil-soluble ammonium alkenyl sulfonates are derived from viscous liquid propene or butene polymers (commonly referred to as polypropenes and polybutenes which are commercially available materials) having a number average molecular weight of about 250–500, by sulfonation with gaseous sulfur trioxide, purification and neutralization with ammonia. Illustrative of the preparation of the ammonium alkenyl sulfonates is the following example:

Liquid polybutene (butene polymer having a number average molecular weight of about 340) was introduced into a slot-type falling-film reactor of the type described in U.S. Pat. No. 3,328,460 at a rate of 388 pounds per hour. The reactor was twenty-two feet long with a slot dimension of ⅜ inch by 24 inches. The film temperature in the reactor was 80°–122° F. Gaseous sulfur trioxide diluted with air at a molar rate of 1.93 mols per mol of polybutene, was introduced cocurrently to the film in the reactor at a rate of 170 pounds per hour and air rate of 900 cubic feet per minute at 18 psig. Liquid residence time was about 125 to 150 seconds in the reactor. The crude acid mix from the reactor had a total activity of about 72 weight percent, contained about 46 weight percent sulfonic acid, about 7 weight percent hexane-insoluble sludge, and about 19 weight percent sultone.

The crude acid mix was diluted with an equal volume of hexane and 10 weight percent water. The aqueous mixture was held with agitation at 130°–140° F. for one hour in a holding-settling tank. After a two-hour settling period, the aqueous phase was drawn off and the hexane-acid phase transferred to a reactor for neutralization.

Neutralization of the sulfonic acid-sultone mixture in hexane was effected by introducing anhydrous ammonia into the mixture at a rate of two cubic feet per hour per gallon while maintaining temperature of the mixture below 150° F. until a color change of from black to amber is noted which indicated neutralization of the sulfonic acid. At that point the ammonia rate was reduced to 0.5 cubic feet per hour per gallon and the temperature of the mixture raised to drive off hexane and water to a temperature of 310° F. The mixture was held at 310° F. with continued introduction of ammonia for two hours to reduce the sultone content at which time the treatment was terminated. The neutralized product containing 64.6 weight percent ammonium alkenyl sulfonate and 2.8 weight percent sultone was a crystal clear liquid that did not require filtration.

The term "activity" as used herein refers to the percent of acidic polar material present in the crude sulfonation reaction and neutralized products by silica gel chromotography. A two-gram sample is diluted with 20 ml. hexane and deposited at room temperature on a 40 gram silica gel column having a 0.75 inch diameter. The unreacted polymer is eluted from the column with 250 ml. of hexane and weight obtained after evaporation of hexane. Sample weight minus weight of polymer yields total activity in sample. Sultone content is obtained by elution with 250 ml of chloroform. Sulfonate content is total activity minus sultone.

Sulfonic acids and the ammonium and/or magnesium salts thereof suitably used in accordance with this invention are oil-soluble sulfonic acids. Such sulfonic acids include oil-soluble petroleum sulfonic acids, commonly referred to as "mahogany acids," alkyl sulfonic acids, aryl sulfonic acids, and alkaryl sulfonic acids. and alkaryl sulfonic acids. Illustrative of suitable sulfonic acids are the oil-soluble petroleum sulfonic acids, e.g. "mahogany acids" of about 350 to 750 molecular weight, dilauryl aryl sulfonic acid, lauryl-cetyl aryl sulfonic acid, paraffin wax-substituted benzene sulfonic acids, didodecyl benzene sulfonic acids, polyolefin alkylated benzene sulfonic acids, such as polybutylene alkylated benzene sulfonic acids, in which the polybutylene substituents have molecular weights of at least about 200, and preferably within the range of from about 300 to about 2500; polypropylene alkylated benzene sulfonic acids in which the polypropylene substituents have a molecular weight of at least about 250, and preferably within the range of from about 290 to about 1500; naphthalene sulfonic acids; alkyl-substituted naphthalene sulfonic acids; and the above described ammonium alkenyl sulfonates.

DESCRIPTION OF THE PREFERRED EMBODIMENTS

EXAMPLE 1

To an oil solution containing 406 grams (0.6 mol) of a petroleum sulfonic acid having an equivalent weight of 592 and containing about 4% sulfuric acid was added 174 gram of 5-W grade mineral oil, 500 ml xylene, 10 gram calcium oxide and 65 ml water. The mixture was stirred for 15 minutes at 75°–85° F. for neutralization of the residual sulfuric acid. Anhydrous ammonia was then introduced into the solution at a rate of 1.6 cubic feet per hour (equivalent to 1.88 mols ammonia per hour) for 10 minutes, thereby forming about 0.3 mol ammonium sulfonate (about 0.1 mol per mol of magnesium oxide) in situ. Then 110 gram magnesium oxide, and 30 ml methanol was added to the solution. The resultant mixture was heated to 180°–190° F. at atmospheric pressure and held under refluxing conditions for one hour at which time the appearance of the mixture was substantially crystal clear indicating that the magnesium oxide had been converted to magnesium hydroxide. The mixture was cooled to 120° F. and gaseous carbon dioxide was introduced at a rate of 1.6 cubic feet per hour (equivalent to 1.88 mols carbon dioxide per hour) while maintaining the temperature of the mixture in the range of 120°–140° F. until the temperature dropped, about 90 minutes, indicating completion of the reaction between carbon dioxide and magnesium hydroxide. The mixture was heated to 340° F. to remove the methanol, water and xylene and then filtered. The product containing about 30% neutral magnesium sulfonate had a total base number (mg KOH/gm) of 336.

EXAMPLE 2

A mixture of a hexane solution of 586 grams (0.4 mol) of a polypropene alkylated benzene sulfonic acid, 350 grams 5-W grade mineral lubricating oil, 6 gram of calcium oxide, and 6 ml water was stirred at room temperature for 30 minutes for residual sulfuric acid neutralization. To the mixture was added gaseous anhydrous ammonia at a rate of 1.6 cubic feet per hour, to neutralize the sulfonic acid and form ammonium sulfonate in situ, until the temperature of mixture dropped 2°–3° F. (about 20 minutes) which indicated completion of the neutralization reaction. The neutralized product mixture was heated to 240° F., while blowing with nitrogen gas, to remove hexane and water and then cooled to 120° F. To the cooled mixture was added 500 ml xylene, 25 ml methanol, 115 gram magnesium oxide and 81 ml water. Reactant mixture was then heated at 180°–190° F., under refluxing conditions, for 90 minutes at which time the mixture had a substantially clear appearance. After cooling the mixture to 100° F., it was blown with gaseous carbon dioxide at a rate of 1.6 cubic feet hour, while maintaining temperature about 120°–130° F., until the temperature dropped 2° F. (completion of carbonation reaction), about 105 minutes. The carbonated mixture was heated to 340° F. to remove methanol, xylene, and water and then filtered. The crystal clear over-based magnesium sulfonate product in mineral oil carrier had a total base number of 333.

EXAMPLE 3

A mixture of 390 gram (0.6 mol) of an oil-soluble ammonium alkenyl sulfonate wherein the alkenyl moiety is a butene polymer having a number average mol weight of about 340, prepared as described above, 240 gram of 5-W mineral lubricating oil, 110 gram magnesium oxide, 700 ml xylene, 76 ml water (1.7 mol water/mol magnesium oxide) and 30 ml methanol was heated at atmospheric pressure and at a temperature of 180°–190° F., under refluxing conditions, for 90 minutes, at which time the mixture had a crystal clear appearance. The mixture was cooled to 100° F. and blown with gaseous carbon dioxide at a rate of 1.6 cubic feet per hour for 90 minutes at which time mixture temperature dropped 2° F. The methanol, water and xylene were removed by heating the carbonated product mixture to 340° F. and filtered. A crystal clear product in mineral oil containing 30% neutral oil-soluble magnesium alkenyl sulfonate had a total base number of 320.

We claim:

1. The method of preparing over-based oil-soluble magnesium sulfonate compositions consisting of the steps of: (I) heating a reactant mixture consisting of (a) an amount of an oil-soluble sulfonate anion-affording material sufficient to provide about 10–14 weight percent oil-soluble magnesium sulfonate in said composition, said material containing molar proportions of about 0.1–1.0 mol oil-soluble ammonium sulfonate, 0 to about 0.9 mol neutral oil-soluble magnesium sulfonate, and 0 to about 0.9 mol oil-soluble sulfonic acid, said reactant (a) further characterized as containing at least 0.1 mol of said ammonium sulfonate per mol of magnesium oxide in said mixture, (b) magnesium oxide in excess of the stoichiometric amount required for neutral magnesium sulfonate formation, (c) about 0.2 to about 1.0 mol of methanol per mol of magnesium oxide, (d) about 0.5 to about 2.25 mols water per mol of magnesium oxide, and (e) an inert hydrocarbon diluent, at a temperature in the range of about 175° F. to 200° F. under refluxing conditions at atmospheric pressure for a period of time sufficient to convert said magnesium oxide to magnesium hydroxide in said mixture; (II) then treating the mixture of step I at a temperature in the range of from about 100° F. to about 160° F. with carbon dioxide until reaction with said magnesium hydroxide ceases; and (III) thereafter removing volatile and unreacted materials from the carbonated mixture.

2. The process of claim 1 wherein said inert hydrocarbon diluent is low viscosity mineral oil and xylene.

3. The process of claim 2 wherein reactant (a) is a mixture of ammonium petroleum sulfonate and petroleum sulfonic acid, said mixture containing about 0.1 mol ammonium sulfonate per mol of magnesium oxide, (b) is about 2.5 mols, (c) is about 0.27 mol, and (d) is about 1.3 moles; and said carbonated mixture is heated to about 340° F. to remove water, methanol and xylene, and thereafter filtered.

4. The process of claim 2 wherein reactant (a) is ammonium sulfonate.

5. The process of claim 4 wherein said sulfonate is an alkyl benzene sulfonate.

6. The process of claim 5 wherein said sulfonate is polypropylene alkylated benzene sulfonate, (b) is about 2.7 mols, (c) is about 0.2 mol, and (d) is about 1.6 mol; and said carbonated mixture is heated to about 340° F. to remove water, methanol and xylene, and thereafter filtered.

7. The process of claim 4 wherein said sulfonate is an ammonium alkenyl sulfonate wherein the alkenyl moiety is a propene or butene polymer having a number average molecular weight of about 250–500.

8. The process of claim 7 wherein said polymer is a butene polymer having a number average molecular weight of about 340, (b) is about 2.5 mols, (c) is about 0.27 mol, and (d) is about 1.7 mols; and said carbonated mixture is heated to about 340° F. to remove water, methanol and xylene, and thereafter filtered.

* * * * *

UNITED STATES PATENT OFFICE
CERTIFICATE OF CORRECTION

Patent No. 4,201,682            Dated May 6, 1980

Inventor(s) Albert R. Sabol, Dennis G. Petrille, and Edward W. Heffern

It is certified that error appears in the above-identified patent and that said Letters Patent are hereby corrected as shown below:

| Patent Column | Line | | |
|---|---|---|---|
| 1 | 14 | "a" should be | --as-- |
| 2 | 25 | "capacity" should be | --opacity-- |
| 2 | 66 | "cocurrently" should be | --concurrently-- |
| 4 | 57 | "feet hour" should be | --feet per hour-- |
| 5 | 3-4 | "1.7 mol water/-mol...)" should be | --(1.7 mol water/mol...)-- |
| 5 | 21 | "10-i4" should be | --10-40-- |

Signed and Sealed this

First Day of September 1981

[SEAL]

Attest:

Attesting Officer

GERALD J. MOSSINGHOFF

Commissioner of Patents and Trademarks